(12) United States Patent
Vermeiren et al.

(10) Patent No.: US 11,445,312 B2
(45) Date of Patent: Sep. 13, 2022

(54) HYBRID ELECTRICALLY- AND MECHANICALLY-STIMULATING COCHLEAR IMPLANT

(71) Applicant: Cochlear Limited, Macquarie University (AU)

(72) Inventors: Jan Vermeiren, Mechelen (BE); Kristof Buytaert, Mechelen (BE); Rishubh Verma, Mechelen (BE)

(73) Assignee: Cochlear Limited, Macquarie University (AU)

( * ) Notice: Subject to any disclaimer, the term of this patent is extended or adjusted under 35 U.S.C. 154(b) by 139 days.

(21) Appl. No.: 16/745,942

(22) Filed: Jan. 17, 2020

(65) Prior Publication Data

US 2020/0260200 A1    Aug. 13, 2020

Related U.S. Application Data

(63) Continuation of application No. 15/416,765, filed on Jan. 26, 2017, now Pat. No. 10,560,791.

(60) Provisional application No. 62/289,003, filed on Jan. 29, 2016.

(51) Int. Cl.
*H04R 25/00* (2006.01)
*A61N 1/05* (2006.01)
*A61N 1/36* (2006.01)

(52) U.S. Cl.
CPC ......... *H04R 25/606* (2013.01); *A61N 1/0541* (2013.01); *A61N 1/36038* (2017.08); *H04R 2225/67* (2013.01); *H04R 2460/13* (2013.01)

(58) Field of Classification Search
CPC .............. A61N 1/36038; A61N 1/0541; H04R 25/606; H04R 2225/67; H04R 2460/13
See application file for complete search history.

(56) References Cited

U.S. PATENT DOCUMENTS

| | | | |
|---|---|---|---|
| 6,231,604 B1 * | 5/2001 | von Ilberg | A61N 1/36038 623/10 |
| 6,636,768 B1 * | 10/2003 | Harrison | A61N 1/36038 607/57 |
| 7,039,466 B1 | 5/2006 | Harrison et al. | |
| 8,128,551 B2 | 3/2012 | Jolly | |
| 9,731,142 B2 | 8/2017 | Mauger et al. | |
| 9,973,865 B2 * | 5/2018 | Francart | H04R 25/356 |
| 10,560,791 B2 | 2/2020 | Vermeiren et al. | |
| 2001/0031996 A1 * | 10/2001 | Leysieffer | A61N 1/36038 607/57 |
| 2004/0133250 A1 * | 7/2004 | Ball | A61N 1/36038 607/57 |
| 2010/0048983 A1 * | 2/2010 | Ball | A61N 1/36036 600/25 |
| 2012/0303097 A1 | 11/2012 | Bernhard et al. | |
| 2014/0228669 A1 | 8/2014 | Carter | |
| 2016/0213943 A1 * | 7/2016 | Mauger | A61N 2/006 |

(Continued)

*Primary Examiner* — Catherine M Voorhees
*Assistant Examiner* — Roland Dinga
(74) *Attorney, Agent, or Firm* — Edell, Shapiro & Finnan, LLC

(57) ABSTRACT

Wires and coils within an electrode assembly electromagnetically interact and cause mechanical motion of the assembly. This mechanical motion can be used to supplement or replace the electrical stimulation provided by a standard cochlear implant and provides targeted acoustic stimulation to the cochlea.

18 Claims, 8 Drawing Sheets

(56) References Cited

U.S. PATENT DOCUMENTS

2017/0120044 A1\* 5/2017 Pawsey ................ A61N 1/0541
2018/0056067 A1\* 3/2018 Leigh ................. A61N 1/36017

\* cited by examiner

HYBRID ELECTRICALLY- AND MECHANICALLY-STIMULATING COCHLEAR IMPLANT

CROSS REFERENCE TO RELATED APPLICATION

This application is a continuation of U.S. application Ser. No. 15/416,765, titled HYBRID ELECTRICALLY- AND MECHANICALLY-STIMULATING COCHLEAR IMPLANT, filed on Jan. 26, 2017, that claims priority to U.S. Provisional Application No. 62/289,003, titled HYBRID ELECTRICALLY- AND MECHANICALLY-STIMULATING COCHLEAR IMPLANT, filed on Jan. 29, 2016, the disclosure of which are hereby incorporated by reference in their entirety.

BACKGROUND

Hearing loss, which can be due to many different causes, is generally of two types: conductive and sensorineural. In many people who are profoundly deaf, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem implants might also be proposed when a recipient experiences sensorineural hearing loss if the auditory nerve, which sends signals from the cochlear to the brain, is severed or not functional.

Conductive hearing loss occurs when the normal mechanical pathways that provide sound to hair cells in the cochlea are impeded, for example, by damage to the ossicular chain or the ear canal. Individuals suffering from conductive hearing loss can retain some form of residual hearing because some or all of the hair cells in the cochlea function normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and can be suitable for individuals who cannot derive sufficient benefit from conventional hearing aids.

SUMMARY

The cochlea is a spiral shaped structure and is tonotopically arranged such that lower frequencies are picked up by nerves at the apex of the cochlear and higher frequencies stimulate nerves at the base. In a cochlear implant, a standard intra-cochlear stimulating assembly thereof includes multiple wires that conduct electrical signals to each of the electrode pads on the assembly. These pads provide electrical stimulation to the cochlea nerves and therefore provide hearing. The technologies described herein use wires and coils within a stimulating assembly to electromagnetically interact and cause mechanical motion of the assembly. This mechanical motion can be used to supplement the electrical stimulation and provide targeted acoustic stimulation to the cochlea. Low frequency acoustic stimulation can be achieved by disposing the coils proximate the tip of the assembly.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Figure 1:
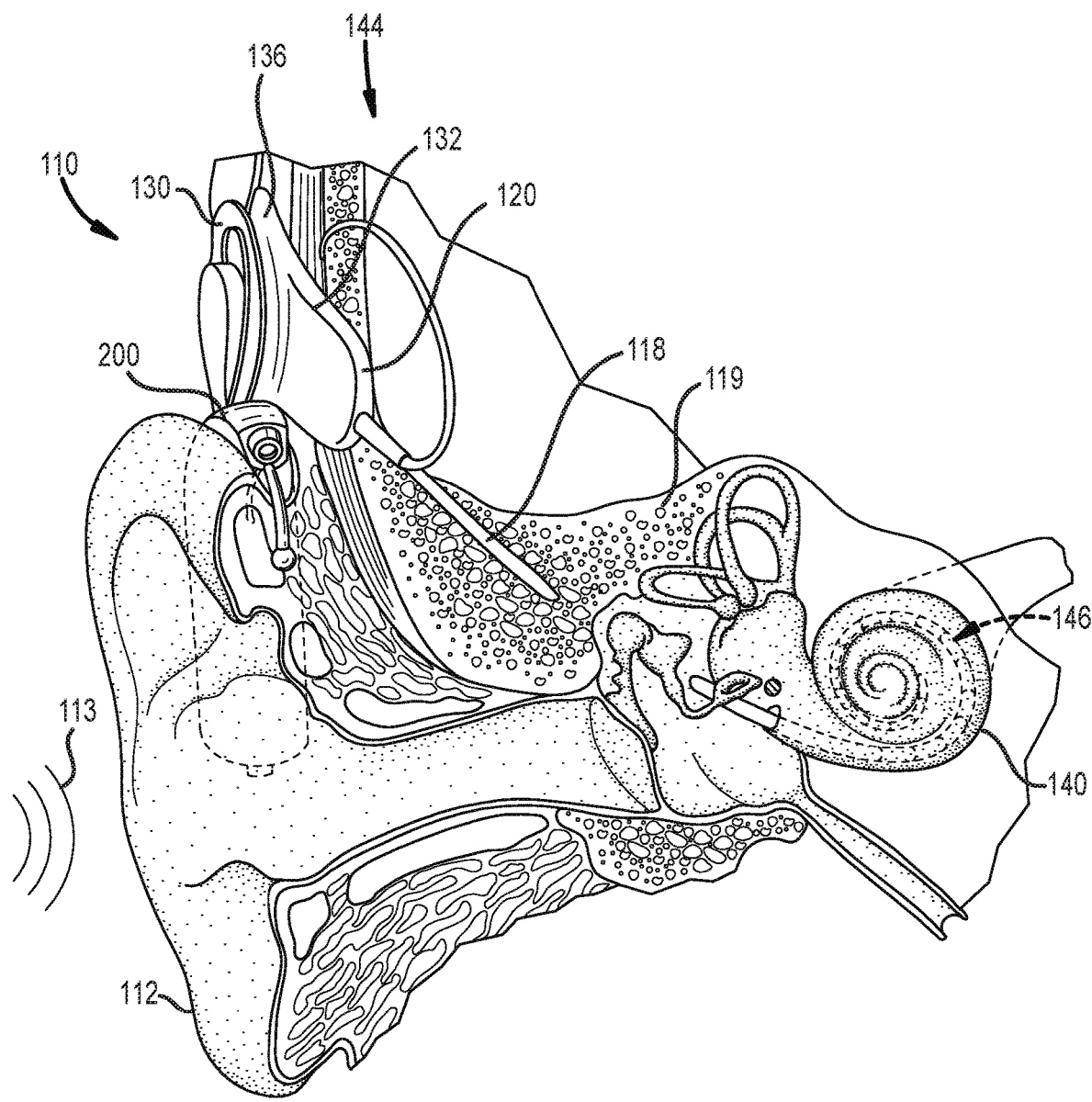
FIG. 1 is a partial view of a behind-the-ear auditory prosthesis worn on a recipient.

Referring to FIG. 1, cochlear implant system 100 includes an implantable component 144 typically having an internal receiver/transceiver unit 132, a stimulator unit 120, and an elongate lead 118. The internal receiver/transceiver unit 132 permits the cochlear implant system 110 to receive and/or transmit signals to an external device. The external device may be a button sound processor worn on the head that includes a receiver/transceiver coil and sound processing components, a receiver/transceiver coil in communication with a BTE device that includes the sound processing components and microphone, a charger for a totally implantable device (such as a totally implantable cochlear implant or middle ear implant), a clinical diagnostic system or any other component capable of exchanging power and/or data signals with the implantable component 144.

The implantable component 144 includes an internal coil 136, and preferably, a magnet (not shown) fixed relative to the internal coil 136. The magnets facilitate the operational alignment of the external and internal coils, enabling internal coil 136 to receive power and stimulation data from external coil 130. The external coil 130 is contained within an external portion 150.

Internal receiver unit 132 and stimulator unit 120 are hermetically sealed within a biocompatible housing, sometimes collectively referred to as a stimulator/receiver unit. The stimulator/receiver unit receives power and/or data signals from external device and produces stimulation signals that are transmitted via an elongate lead 118 to the cochlea 140. Elongate lead 118 has a proximal end connected to stimulator unit 120, and a distal end implanted in cochlea 140. Elongate lead 118 extends from stimulator unit 120 to cochlea 140 through mastoid bone 119.

In certain examples, external coil 130 transmits electrical signals (e.g., power and stimulation data) to internal coil 136 via a radio frequency (RF) link, as noted above. Internal coil 136 is typically a wire antenna coil comprised of multiple turns of electrically insulated single-strand or multi-strand platinum or gold wire. The electrical insulation of internal coil 136 is provided by a flexible silicone molding. Various types of energy transfer, such as infrared (IR), electromagnetic, capacitive and inductive transfer, can be used to transfer the power and/or data from external device to cochlear implant.

Figure 2:
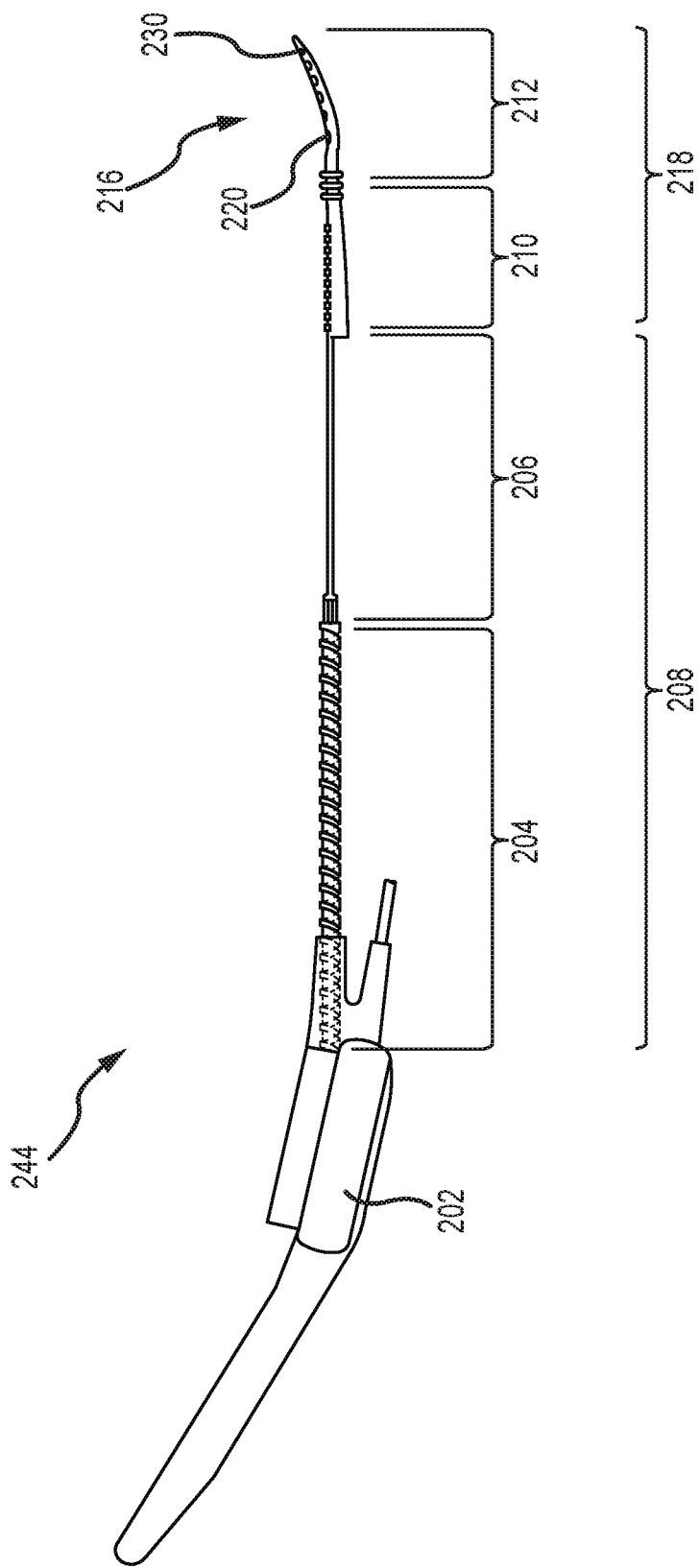
FIG. 2 is a side view of an example of an implantable portion of an auditory prosthesis.

FIG. 2 is a simplified side view of an internal component 244 having a stimulator/receiver unit 202 which receives encoded signals from an external component of the cochlear implant system. Internal component 244 terminates in a stimulating assembly 218 that comprises an extra-cochlear region 210 and an intra-cochlear region 212. Intra-cochlear region 212 is configured to be implanted in the recipient's cochlea and has disposed thereon a contact array 216. In the depicted example, contact array 216 comprises both optical contacts 220 and electrical contacts 230.

There are a variety of types of intra-cochlear stimulating assemblies including short, straight and perimodiolar. For example, lateral wall array stimulating assemblies that sit, after implantation, in the cochlea away from the modiolus can be used with the technologies described herein. The depicted peri-modiolar stimulating assembly 218 is configured to adopt a curved configuration during and or after implantation into the recipient's cochlea. To achieve this, in certain arrangements, stimulating assembly 218 is pre-curved to the same general curvature of a cochlea. Such examples of stimulating assembly 218, are typically held straight by, for example, a stiffening stylet (not shown) or sheath which is removed during implantation, or alternatively varying material combinations or the use of shape memory materials, so that the stimulating assembly can adopt its curved configuration when in the cochlea. Other methods of implantation, as well as other stimulating assemblies which adopt a curved configuration, can be used and are described herein.

Stimulating assembly 218 can also be a non-perimodiolar stimulating assembly. For example, stimulating assembly 218 can include a straight stimulating assembly or a mid-scala assembly which assumes a midscala position during or following implantation.

Alternatively, the stimulating assembly can be a short electrode implanted into at least in basal region. The stimulating assembly can extend towards apical end of cochlea, referred to as cochlea apex. In certain circumstances, the stimulating assembly can be inserted into cochlea via a cochleostomy. In other circumstances, a cochleostomy can be formed through round window, oval window, the promontory or through an apical turn of cochlea.

Internal component 244 further comprises a lead region 208 coupling stimulator/receiver unit 202 to stimulating assembly 218. Lead region 208 comprises a region 204 which is commonly referred to as a helix region, however, the required property is that the lead accommodate movement and is flexible, it does not need to be formed from wire wound helically. Lead region also comprises a transition region 206 which connects helix region 204 to stimulating assembly 218. As described below, optical and/or electrical stimulation signals generated by stimulator/receiver unit 202 are delivered to contact array 216 via lead region 208. Helix region 204 prevents lead region 208 and its connection to stimulator/receiver 202 and stimulating assembly 218 from being damaged due to movement of internal component 244 (or part of 244) which can occur, for example, during mastication.

Figure 3:
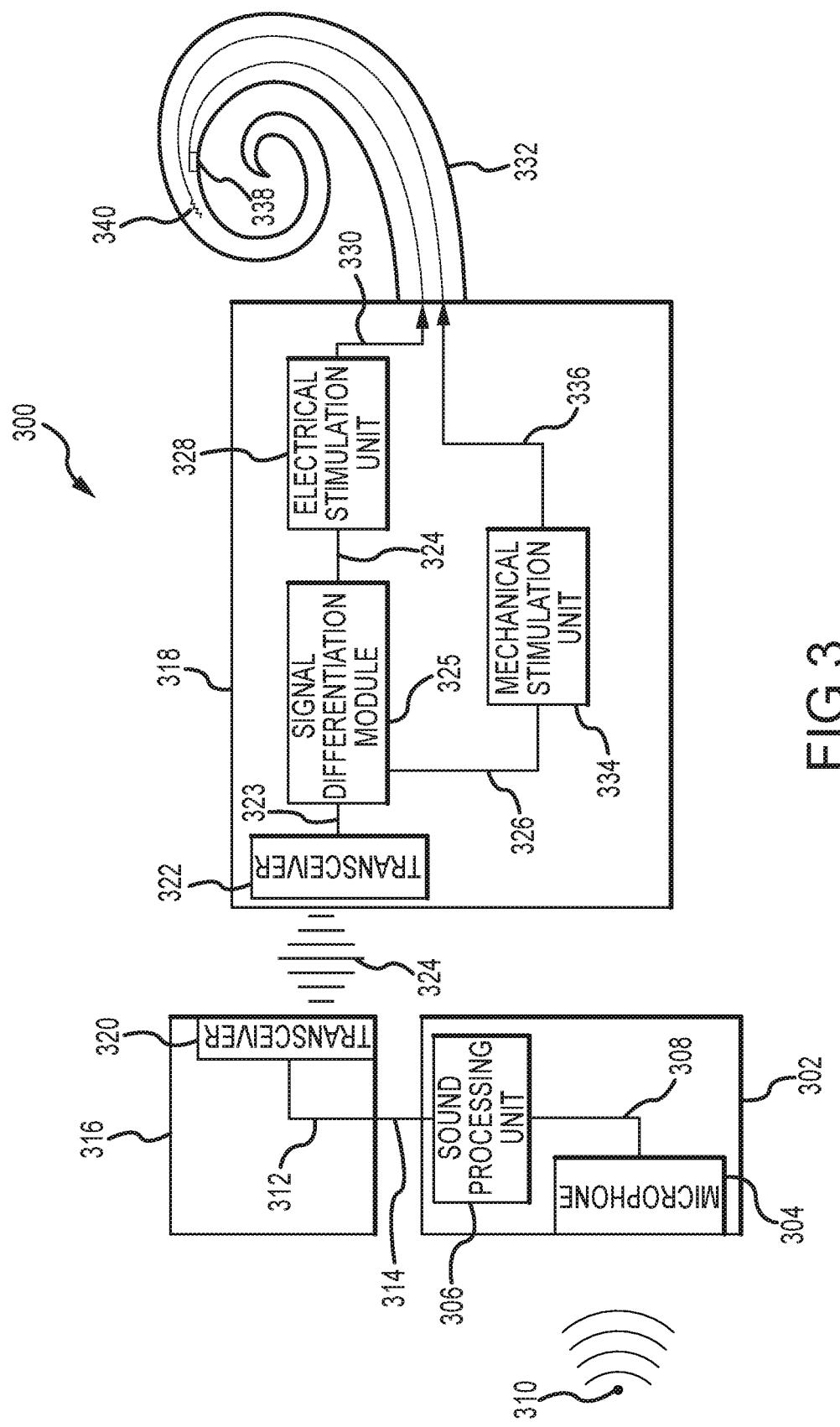
FIG. 3 is a schematic diagram of a hybrid electrically- and mechanically-stimulating cochlear implant.

FIG. 3 is a schematic diagram of a hybrid electrically- and mechanically-stimulating cochlear implant auditory prosthesis 300. The prosthesis 300 is a cochlear implant having implantable and external portions, as described elsewhere herein. As such, not all components are necessarily described. A behind-the-ear (BTE) portion 302 contains a microphone 304 and a sound processing unit 306. An electrical signal 308 representing a sound signal 310 detected by the microphone 304 is provided from the microphone 304 to the sound processing unit 306. The sound processing unit 306 implements one or more sound processing and/or coding strategies to convert the pre-processed microphone output into data signals 312. The data signals 312 are sent via a tethered cable 314 to an external portion 316 of the prosthesis 300. The external portion 316 is held in contact with an implantable portion 318 via a magnetic retention force. A transceiver 320 in the external portion 316 communicates with a corresponding transceiver 322 in the implantable portion 318. Signals 323 received by the implantable transceiver 322 are routed to one of two stimulation units within the implantable portion 318, via a signal differentiation module 325. The signal differentiation module 325 is configured to identify the incoming signals 323 and send the appropriate signals 324, 326 to the appropriate stimulation unit. A first, or electrical, stimulation unit 328 generates electrical stimulation signals 330 for delivery to the cochlea of the recipient, via a hybrid stimulating assembly 332. A second, or mechanical, stimulation unit 334 generates electrical stimulation signals 336 for delivery to the cochlea of the recipient, again via the hybrid stimulating assembly 332.

The electrical stimulation unit 328 and the mechanical stimulation unit 334 both deliver electrical stimulation signals 330, 336 to the recipient. The signals 330, 336, however, have different characteristics and are connected to different stimulators within the hybrid stimulating assembly 332. The signals 330 are delivered via one or more electrodes 338 within the hybrid assembly 332, as with the cochlear implants described above. A discrete electrode 338 acts as an electrical stimulator, delivering electrical stimuli directly to the cochlea. In examples, the signals 330 are delivered directly into the cochlea. The signals 336 are delivered to one or more coils 340 within the hybrid assembly 332. The coils (and any associated magnets, as described below) act as a mechanical stimulator delivering mechanical stimuli directly to the cochlea. These signals 336 are pass through the coil(s) 340 to cause the hybrid stimulating assembly 332 to expand and contract (or stretch and return). In examples, the coil(s) 340 can be manufactured of a biocompatible material such as platinum, or can be embedded in a rigid biocompatible material such as polyether ether ketone (PEEK), polyphenylsulfone (PPSU), or other comparable rigid plastics. As described below, in certain examples, magnets are used in conjunction with the coils 340. Those magnets may also be embedded in a biocompatible material, such as those described above. In other examples, the signals can cause the hybrid assembly 332 to vibrate within the cochlea or otherwise deform. The deformation and/or vibration provides mechanical stimulation to the recipient through acoustic waves that travel toward the apical end of the cochlea through the perilymph. Certain contemplated embodiments of hybrid electrode assemblies are further described below.

Cochlear implants that deliver both electrical stimulation and mechanical stimulation, such as those described herein, can be utilized in a variety of configurations. For example, conventional cochlear implants can have up to twenty-two electrodes for delivery of stimuli to a recipient, each delivering a signal associated with a specific received sound frequency range. The stimulus is typically in the form of electrical stimuli delivered directly to the cochlea/nerve. The coils utilized in the hybrid systems described herein can replace one or more of these electrodes, or can be used to supplement the output of one or more electrodes. In examples, the mechanical stimulus produced by the coil movement can be on a lower range of the audible human frequency, such as below 2 kHz, 1.5 kHz or 1 kHz. Low frequency mechanical stimulation can be used in conjunction with a short electrode array that is implanted in the basal region of the cochlea (i.e. not past the basal turn) to help preserve low frequency hearing. The electrical contacts on the electrode array can stimulate a high frequency range not stimulated acoustically.

Mechanical stimulation to the cochlea can be desirable for recipients who have retained some measure of residual hearing. These recipients typically retain such hearing at very low frequencies. The mechanical stimulation creates a wave within the cochlea fluid that resonates within the cochlea at particular frequencies, for example, the residual lower frequencies. The mechanical stimulation, then, lends itself more desirably to the use of straight stimulating arrays. Since the stimulating array expands and contracts within the cochlea (as described in more detail below), straight assemblies that to not penetrate deep into the cochlea may be desirable, since they can be inserted so as not to contact the basilar membrane of the cochlea. Contact between the stimulating assembly and basilar membrane can reduce the efficacy of the mechanical stimulation by impeding vibration or can damage the membrane structure. Additionally, straight assemblies can be more desirable since they can retain the residual hearing, again because they are not inserted as deeply into the cochlea. Regardless, curved stimulating assemblies can be utilized with the present technology in certain applications.

Mechanical stimulation to the cochlea can have other advantages. With electrical stimulation provided by electrodes within a cochlear implant, there are often overlaps in frequency ranges produced by the various electrodes, or gaps between the frequency ranges of adjacent electrodes. Mechanical stimulation, however, can produce a finer spectrum of sound, thereby eliminating or reducing such gaps and overlaps in situations where the recipient retains some residual hearing. Additionally, mechanical stimulation can be better suited to delivering lower frequencies within the hearing spectrum. Certain embodiments of the hybrid systems, then, can utilize mechanical stimulation for received sounds lower than about 1 kHz. Electrical stimulation can be used to deliver signals to the cochlea for sounds in excess of 1 kHz. Additionally, the mechanical stimulators incorporated into the stimulating assemblies described herein can be positioned based on their associated sound frequency. That is, mechanical stimulators that are configured to deliver stimuli associated with lower frequency signals can be disposed more apically within the cochlea, toward a distal end of the intra-cochlear region. Mechanical stimulators that are configured to deliver stimuli associated with higher frequency signals can be disposed more basally within the cochlea, toward a proximal end of the intra-cochlear region.

Figure 4:
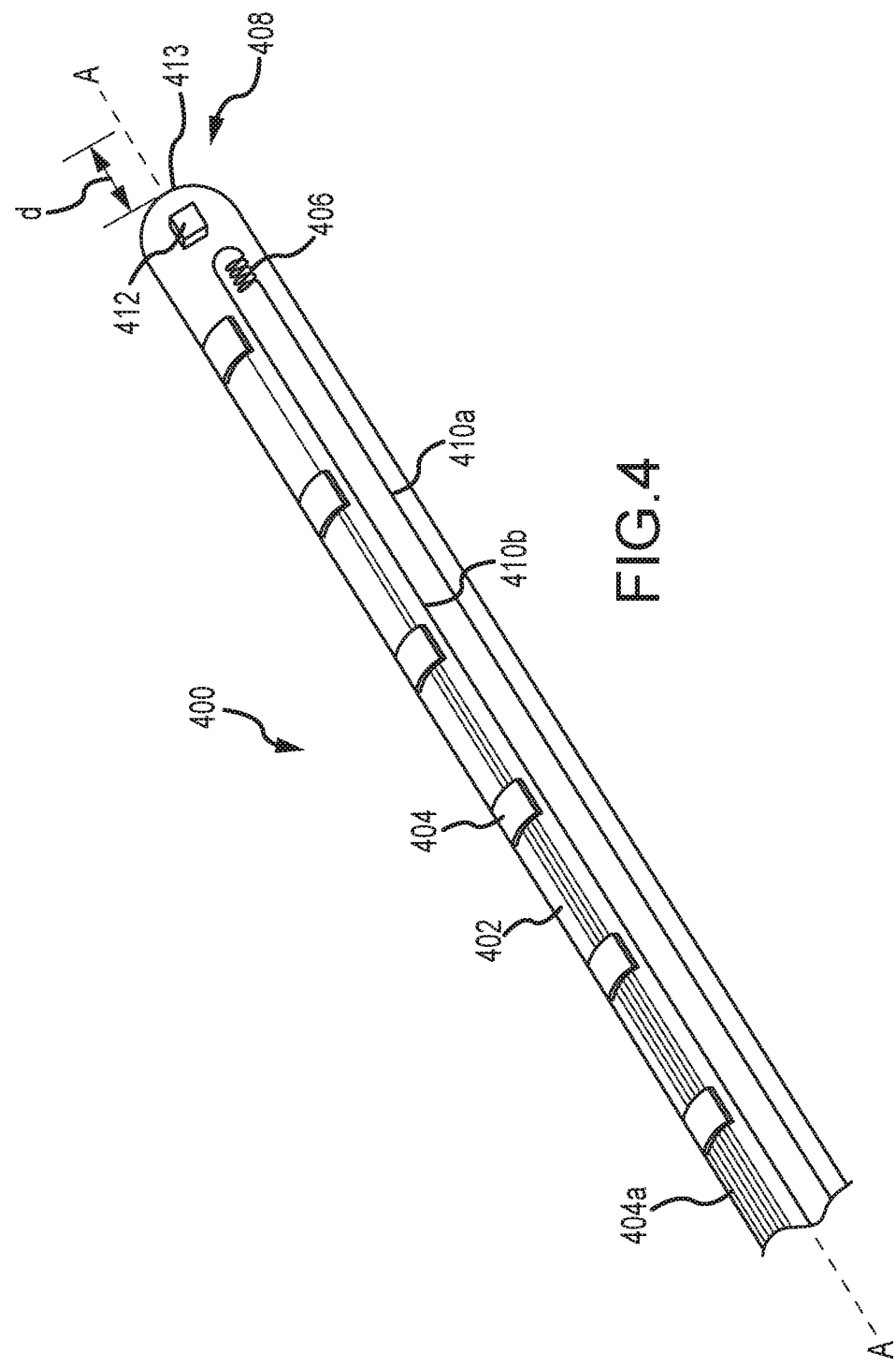
FIGS. 4-7 are partial schematic views of intra-cochlear regions of hybrid stimulating assemblies.

FIG. 4 is a partial schematic view of an intra-cochlear region 400 of a hybrid stimulating assembly. The intra-cochlear region 400 includes an elongate carrier 402 that is depicted in a straight configuration, having an axis A, for clarity. This region 400 includes a number of electrodes 404 disposed on the surface thereof. Each electrode 404 is connected to the electrical stimulation unit of FIG. 3 via a pair of discrete leads or wires 404a (only one of which is shown for clarity). The intra-cochlear region 400 also includes a coil 406 disposed proximate a tip 408 thereof. Leads or wires 410a, 410b connect the coil 406 to the mechanical stimulation unit of FIG. 3. A piece of magnetic material 412 is disposed proximate the coil 406. More specifically, the magnetic material 412 can be disposed between the coil 406 and the terminus 413 of the region 400. The magnetic material 412 and coil 406 that form the mechanical stimulator are disposed between the most distal electrode 404 and the terminus 413. The magnetic material 412 can be a rare earth or other magnet. In examples, a neodymium magnet can be utilized. When an electrical signal is sent via the wires 410a, 410b, the flux generated at the coil 406 moves the magnet 412 back and forth within the carrier 402. As such, the coil 406 and magnetic material 412 function as a magnetic induction assembly and, upon receipt of the electrical signal at the coil 406, deform the carrier 402. In examples, where the loops of the coil 406 are disposed generally about the axis A, the movement of the magnet 412 is substantially axially along axis A. Since the carrier 402 is a generally flexible material, such as silicone, movement of the magnet 412 causes an axial stretching and deformation of the carrier 402. The maximum deformation may be a distance d, and can be proportional to the frequency of the signal sent along wires 410a, 410b. In examples, the total deformation can be up to about 10 microns. In certain examples, relative higher frequencies will stretch the carrier 402 less than relatively lower frequencies. The total stretch, and therefore total stimulation provided therefrom, can be dependent on a number of factors. Such factors include, but are not limited to, the resistance of the wires, electrical signal being delivered, the durometer of the silicone carrier, the number of turns on the coils, the magnetic strength of the magnet, and so on.

Figure 5:
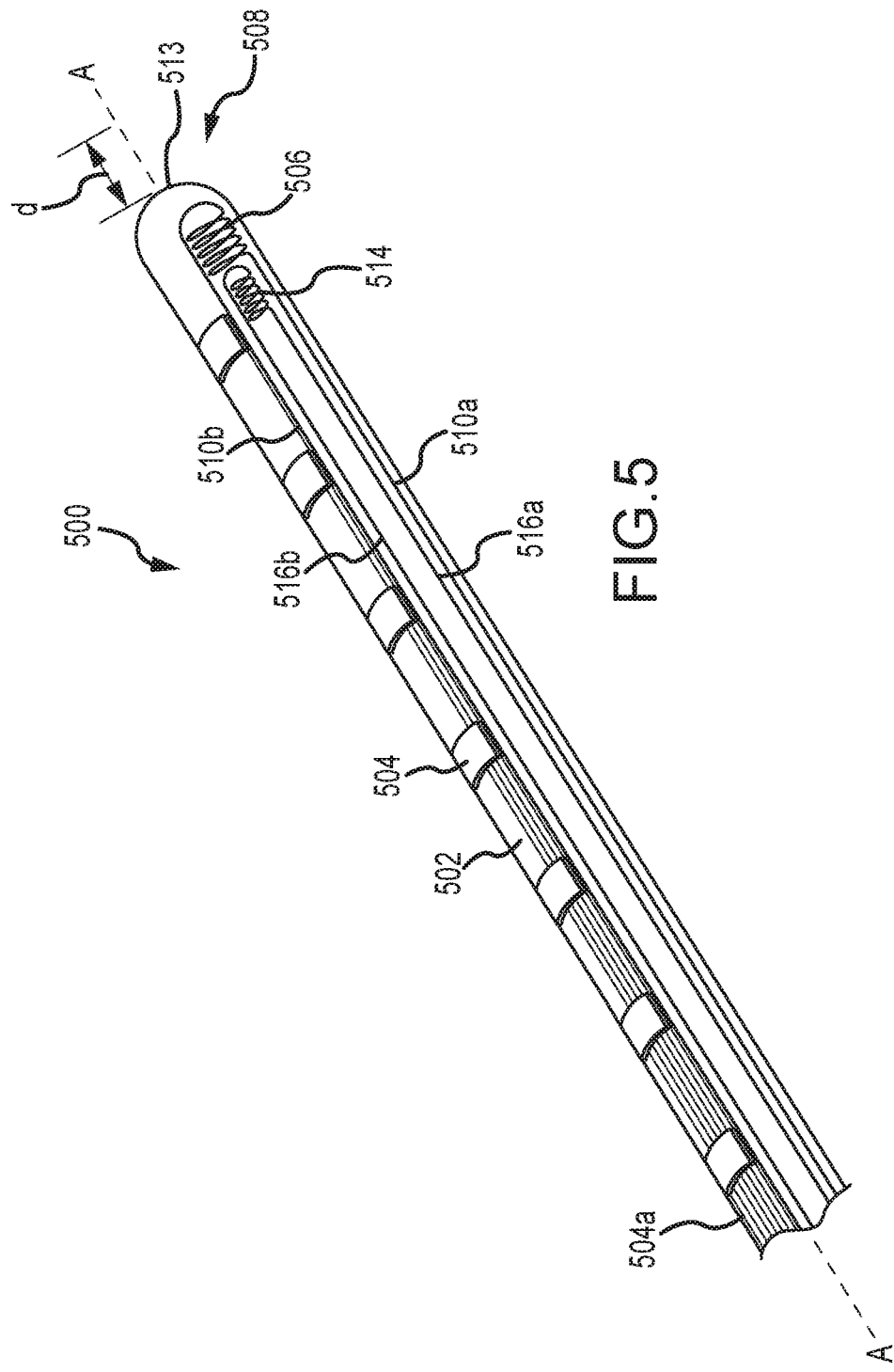

FIG. 5 is a partial schematic view of an intra-cochlear region 500 of a hybrid stimulating assembly. The intra-cochlear region 500 includes an elongate carrier 502 that is depicted in a straight configuration, having an axis A. This region 500 includes a number of electrodes 504 disposed on the surface thereof. Each electrode 504 is connected to the electrical stimulation unit of FIG. 3 via a pair of discrete leads or wires 504a (only one of which is shown for clarity).

This example includes two coils 506, 514, proximate a tip 508 thereof. Leads or wires 510a, 510b connect the coil 506 to the mechanical stimulation unit of FIG. 3, as above. A second coil 514 is connected to the mechanical stimulation unit of FIG. 3 with leads or wires 516a, 516b. Moreover, the first coil 506 and second coil 514 that form the mechanical stimulator are disposed between the most distal electrode 504 and a terminus 513 of the region 500. Unlike the example of FIG. 4, however, this intra-cochlear region 500 does not utilize any magnetic material. As such, it can be safer for a recipient that is subjected to magnetic resonance imaging (MRI) procedures. When an electrical signal is sent via the associated wires to the coils 506, 514, the flux generated between the two coils 506, 514 moves coils 506, 514 within the carrier 502. In an example, the electrical signal delivered to coil 506 is an electrical current that is out of phase with the electrical current delivered to coil 514. As such, the coils 506, 514 function as a magnetic induction assembly and, upon receipt of these out of phase electrical signals of the coils 506, 514, deform the carrier 502. Where the loops of the coils 506, 514 are disposed generally about the axis A, the movement of the coils 506, 514 is substantially axially along axis A. This movement causes an axial stretching or deformation of the carrier 502. The maximum deformation may be a distance d, and can be proportional to the frequency of the signal sent to the coils 506, 514.

Figure 6:
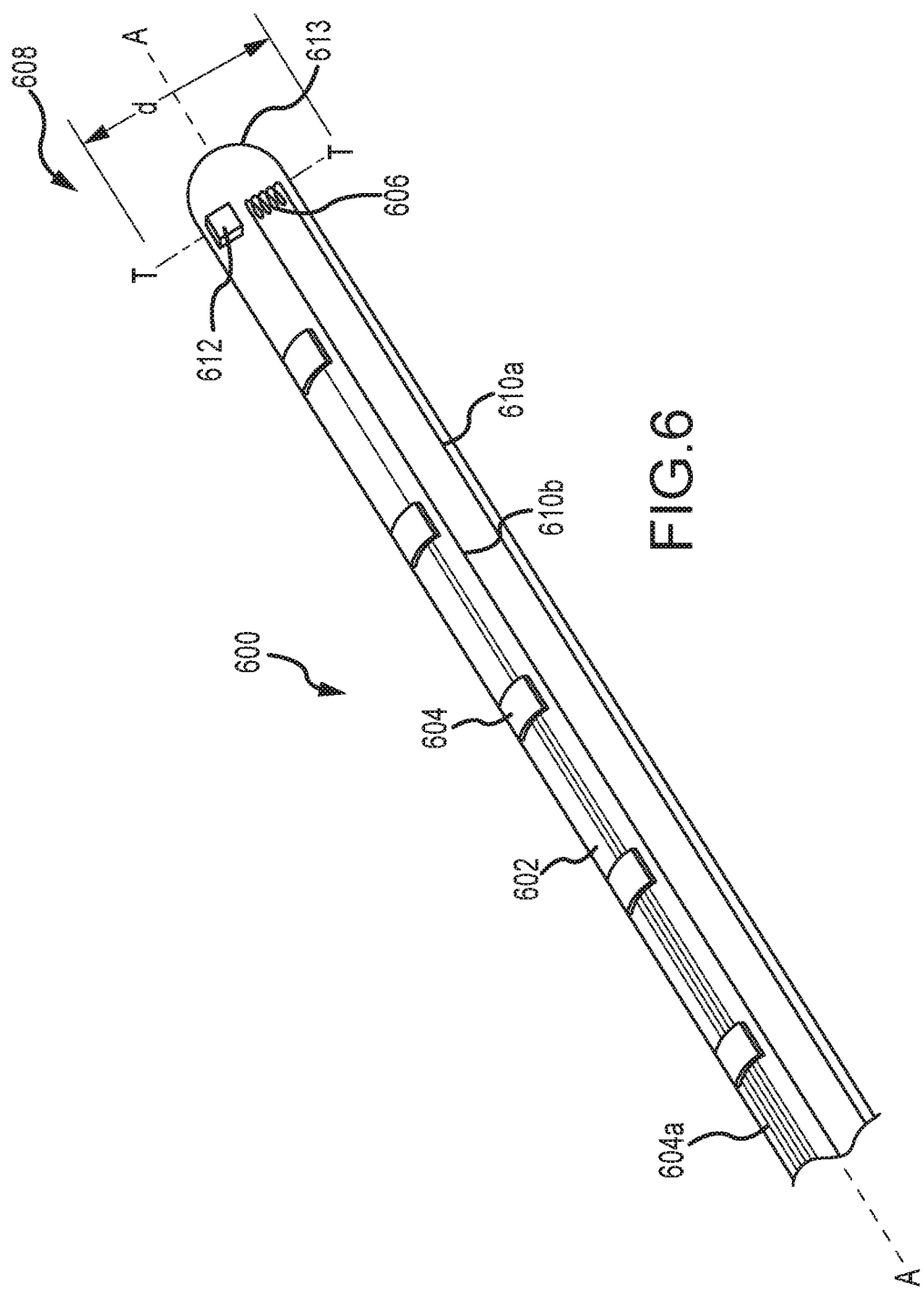

FIG. 6 is a partial schematic view of an intra-cochlear region 600 of a hybrid stimulating assembly. The intra-cochlear region 600 includes an elongate carrier 602 that is depicted in a straight configuration, having an axis A, for clarity. This region 600 includes a number of electrodes 604 disposed on the surface thereof. Each electrode 604 is connected to the electrical stimulation unit of FIG. 3 via a pair of discrete leads or wires 604a (only one of which is shown for clarity). The intra-cochlear region 600 also includes a coil 606 disposed proximate a tip 608 thereof. Leads or wires 610a, 610b connect the coil 606 to the mechanical stimulation unit of FIG. 3. A piece of magnetic material 612 is disposed proximate the coil 606 and forms therewith a magnetic induction assembly. Moreover, the magnetic material 612 and the first coil 606 that form the mechanical stimulator are disposed between the most distal electrode 604 and a terminus 613 of the region 600. When an electrical signal is sent via the wires 610a, 610b, the flux generated at the coil 606 moves the magnet 612 back and forth within the carrier 602. In examples, where the loops of the coil 606 are disposed generally about an axis T that is transverse to the axis A, the movement of the magnet 612 is substantially transverse to axis A. Since the carrier 602 is a generally flexible material, such as silicone, movement of the magnet 612 causes a transverse stretching or deformation of the carrier 602. The maximum deformation may be a distance d, and can be proportional to the frequency of the signal sent along wires 610a, 610b. In certain examples, relative higher frequencies will stretch the carrier 602 less than relatively lower frequencies.

Figure 7:
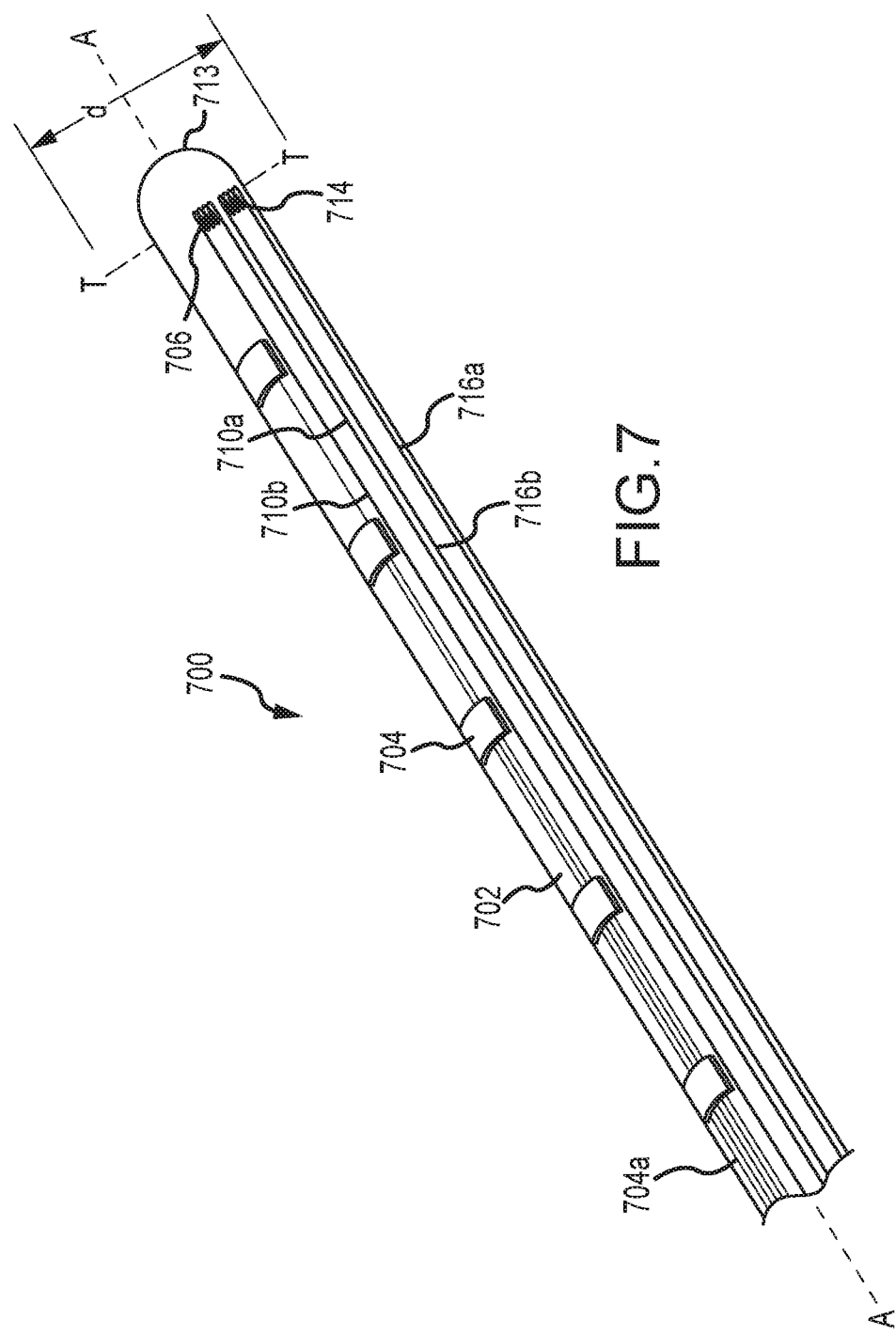

FIG. 7 is a partial schematic view of an intra-cochlear region 700 of a hybrid stimulating assembly. The intra-cochlear region 700 includes an elongate carrier 702 that is depicted in a straight configuration, having an axis A. This region 700 includes a number of electrodes 704 disposed on the surface thereof. Each electrode 704 is connected to the electrical stimulation unit of FIG. 3 via a pair of discrete leads or wires 704a (only one of which is shown for clarity).

Like the example of FIG. 5, this example includes two coils 706, 714, proximate a tip 708 thereof. Leads or wires 710a, 710b connect the coil 706 to the mechanical stimulation unit of FIG. 3, as above. A second coil 714 is connected to the mechanical stimulation unit of FIG. 3 with leads or wires 716a, 716b. Moreover, the first coil 706 and second coil 714 that form the mechanical stimulator (as well as a magnetic induction assembly) are disposed between the most distal electrode 704 and a terminus 713 of the region 700. When an electrical signal (e.g., out of phase currents, as described above) is sent via the associated wires to the coils 706, 714, the flux generated between the two coils 706, 714 moves coils 706, 714 within the carrier 702. Unlike the example of FIG. 5, however, the coils 706, 714 are disposed generally on opposite sides of the axis A, aligned with an axis T that is transverse to axis A, aligned with an axis T that is transverse to axis A. As such, the movement of the coils 706, 714 is substantially transverse or orthogonal to the axis A. This movement causes a transverse stretching or deformation of the carrier 712, which can be defined by a distance d, and can be proportional to the frequency of the signal sent to the coils 706, 714.

The coil configurations of FIGS. 4-7 result in deformation in different directions, based on the configuration of the coil(s) and/or magnetic material. These figures depict the carrier stretching only axially or orthogonally (transversely). It will be apparent, however, that stretching can be in generally any direction (relative to the axis A), depending on the location of the coil(s) and magnet (if used). For example, each of a coil and a magnet can define an angle to the axis A of less than about 90°. Angles of about 45° to about 85° and about 60° to about 75° are contemplated. Other angles can be utilized.

Figure 8:
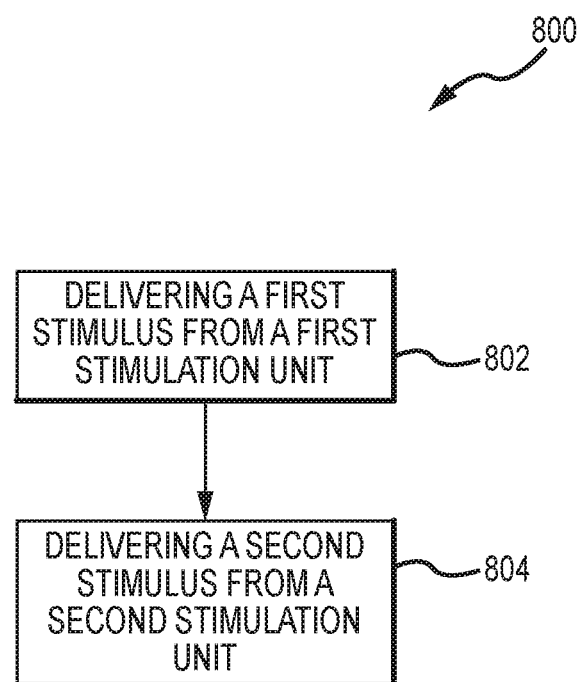
FIG. 8 depicts a method of providing stimuli with a hybrid stimulation assembly.

FIG. 8 depicts a method 800 of providing stimuli with a hybrid electrode assembly, e.g., for a cochlear implant. The method 800 includes delivering a first stimulus from a first stimulation unit, operation 802. This stimulation element can be disposed within an implanted portion of an auditory prosthesis such as a cochlear implant. In operation 804, a second stimulus is delivered from a second stimulation unit. The second stimulus displays a different characteristic than the first stimulus. For example, as described herein, the first stimulus can be a first signal, while the second stimulus can be a second signal different from the first signal. The electrical signal causes a housing of the cochlear implant (more specifically, the stimulating assembly) to deform (e.g., expand and contract or stretch and return), thus delivering a mechanical stimulus to the cochlea of the recipient. Depending on the orientation of the mechanical stimulator within the stimulating assembly, the stretching may be axially along the stimulation assembly, or may be at an angle thereto.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed is:

1. An apparatus comprising:
   an elongate carrier having an intra-cochlear region;
   an electrical stimulator disposed at the intra-cochlear region of the elongate carrier and being configured to deliver an electrical stimulus to a cochlea of a recipient; and
   a mechanical stimulator comprising at least two induction coils encapsulated in the intra-cochlear region of the elongate carrier, wherein the at least two induction coils are configured to deliver mechanical stimulation to the cochlea of the recipient,
   wherein the mechanical stimulator is disposed at the intra-cochlear region such that the mechanical stimulator is located at a basal region of a recipient's cochlea when the elongate carrier is implanted.

2. The apparatus of claim 1, wherein the mechanical stimulator further includes a magnet encapsulated in the elongate carrier.

3. The apparatus of claim 1, wherein the at least two induction coils are aligned along an axis of the elongate carrier.

4. The apparatus of claim 1,
wherein the elongate carrier includes a distal end that terminates at a tip of the elongate carrier;
wherein the electrical stimulator is disposed at a location between the tip and the mechanical stimulator.

5. The apparatus of claim 1, wherein the electrical stimulator comprises a plurality of electrical contacts.

6. The apparatus of claim 1, wherein an electrical signal directed to the mechanical stimulator causes an expansion of the elongate carrier.

7. The apparatus of claim 1, wherein the mechanical stimulator is configured to deliver stimuli associated with lower frequency signals than the electrical stimulator.

8. An apparatus comprising:
an elongate carrier having an intra-cochlear region, wherein the intra-cochlear region comprises a proximal intra-cochlear region and a distal intra-cochlear region;
a mechanical stimulator comprising a first coil and a second coil each encapsulated in the elongate carrier, wherein the first coil and the second coil are disposed within the proximal intra-cochlear region; and
a plurality of electrodes exposed on a surface of the intra-cochlear region.

9. The apparatus of claim 8,
wherein the elongate carrier comprises a flexible body that defines an elongate axis; and
wherein the first coil is substantially axially aligned with the second coil along the elongate axis.

10. The apparatus of claim 8,
wherein the elongate carrier comprises a flexible body that defines an elongate axis, and wherein each of the first coil and the second coil are embedded within the flexible body along a coil axis substantially transverse to the elongate axis.

11. The apparatus of claim 8,
wherein the elongate carrier comprises a flexible body that includes an elongate axis;
wherein each of the first coil and the second coil is configured to receive an electrical current that is out of phase with the electrical current in the other coil; and
wherein receipt of the respective currents causes the elongate carrier to stretch along the elongate axis.

12. The apparatus of claim 8, wherein the mechanical stimulator further comprises a magnet disposed within the elongate carrier.

13. A method comprising:
using a mechanical stimulator that includes two induction coils encapsulated in an elongate carrier to deliver a first stimulus as acoustic waves generated from an intra-cochlear region of a recipient's cochlea toward an apical end of the recipient's cochlea; and
delivering a second stimulus via that is different than the first stimulus.

14. The method of claim 13, wherein the second stimulus is an electrical stimulus.

15. The method of claim 13, wherein the intra-cochlear region does not extend past a basal turn of the recipient's cochlea.

16. The method of claim 13, wherein the first stimulus delivers signals corresponding to sounds less than 2 kHz.

17. The method of claim 16, wherein the first stimulus delivers signals corresponding to sounds less than 1.5 kHz.

18. The method of claim 17, wherein the first stimulus delivers signals corresponding to sounds less than 1 kHz.

\* \* \* \* \*